United States Patent [19]
Kimura et al.

[11] Patent Number: 5,916,422
[45] Date of Patent: Jun. 29, 1999

[54] METHOD OF PURIFYING ACETIC ACID

[75] Inventors: Satoshi Kimura, Niigata; Takashi Ueno, Hyogo; Yoshiaki Morimoto, Niigata, all of Japan

[73] Assignee: Daicel Chemical Industries, Ltd., Osaka, Japan

[21] Appl. No.: 08/813,564

[22] Filed: Mar. 7, 1997

Related U.S. Application Data

[63] Continuation of application No. 08/458,359, Jun. 2, 1995, abandoned.

[30] Foreign Application Priority Data

Aug. 12, 1994 [JP] Japan .................................... 6-190699

[51] Int. Cl.$^6$ ............................. B01D 3/10; C07C 51/44
[52] U.S. Cl. ............................... 203/16; 203/25; 203/27; 203/73; 203/80; 203/DIG. 8; 203/DIG. 21; 562/600; 562/608
[58] Field of Search .................................... 562/517, 600, 562/608; 203/25, 26, 27, DIG. 8, 73, 80, 16, DIG. 21

[56] References Cited

U.S. PATENT DOCUMENTS

| | | | |
|---|---|---|---|
| Re. 34,281 | 6/1993 | Gracey | 203/38 |
| 3,324,010 | 6/1967 | Bauer et al. | 203/1 |
| 3,414,484 | 12/1968 | Carson et al. | 203/26 |
| 4,029,553 | 6/1977 | Price . | |
| 4,039,395 | 8/1977 | Eby . | |
| 4,246,073 | 1/1981 | Umeda et al. | 203/25 |
| 4,381,221 | 4/1983 | Isshiki et al. | 203/6 |
| 4,559,108 | 12/1985 | Ahlberg | 202/154 |
| 4,824,527 | 4/1989 | Erickson | 203/25 |
| 5,227,520 | 7/1993 | Cooper | 562/519 |
| 5,352,415 | 10/1994 | Ochiai | 422/105 |
| 5,391,821 | 2/1995 | Koyama et al. | 562/519 |

FOREIGN PATENT DOCUMENTS

| | | |
|---|---|---|
| 959 183 | 2/1957 | Germany . |
| 42-6243 | 3/1942 | Japan . |
| 47-3334 | 1/1972 | Japan . |
| 48-30615 | 9/1973 | Japan . |
| 60-54334 | 3/1985 | Japan . |
| 1 294 432 | 10/1972 | United Kingdom . |

OTHER PUBLICATIONS

C. Judson King, "Separation Processes", Second Edition, McGraw Hull Book Co. pp. 692–710.
John C. Olsen, "Unit Processes and Principles of Chemical Engineering", N.Y. pp. 1–3.
Derwent Patent Family Data and Abstract for each of the above–identified Japanese references.

*Primary Examiner*—Virginia Manoharan
*Attorney, Agent, or Firm*—Flynn, Thiel, Boutell & Tanis, P.C.

[57] ABSTRACT

A method for purifying acetic acid containing at least one component selected from the group consisting of unsaturated compounds and carbonyl compounds as an impurity involves the step of purifying the acetic acid with a distillation column having at least 30 plates by operating the distillation column at a pressure ranging from 40 to 760 mmHg and a reflux ratio of at least 4, and yields a high-quality acetic acid which rates high in the potassium permanganate test without needing of the addition of any chemical to the acetic acid to be purified and a large amount of energy, and is economical.

13 Claims, 2 Drawing Sheets

METHOD OF PURIFYING ACETIC ACID

This application is a continuation of U.S. Ser. No. 08/458,359, filed Jun. 2, 1995 abandoned.

BACKGROUND OF THE INVENTION

1. Field of the Invention

The present invention relates to an industrial method for purifying acetic acid, particularly to a method for purifying acetic acid obtained by carbonylation of methanol.

2. Description of the Related Art

Acetic acid is a basic chemical employed as a starting material of each of, for example, acetic esters, acetic anhydride, vinyl acetate and terephthalic acid and thus employed in large quantity in the petrochemical, organic chemistry, pharmaceutical and agricultural chemical production, polymer chemistry and other industries.

Various industrial processes are known for producing acetic acid, which include, for example, oxidation of acetaldehyde, direct oxidations of hydrocarbons such as petroleum naphtha and butane, and carbonylation of methanol. Of these, the process in which acetic acid is produced by continuously carbonylating methanol with carbon monoxide (see Japanese Patent Publication-B No. 47-3334) is now widely employed as an industrial process for producing acetic acid.

In recent years, reaction conditions and catalyst improvements have been studied in the above acetic acid production through carbonylation of methanol. For example, a process in which a catalyst stabilizer such as an iodide salt is added to the reaction system has been disclosed [see G.B. Patent Publication-A No. 2,146,637 (published on Apr. 24, 1985)]. In Japanese Patent Publication-A No. 60-54334, it has been proposed to cause a relatively large amount of iodide ions to be present in a reaction fluid so as to lower the concentration of water in the reaction fluid, thereby minimizing the energy required to obtain purified dry acetic acid per unit quantity thereof and further omitting a purification process for obtaining acetic acid as a product [see European Patent Publication-A No. 573,189 (published on Dec. 8, 1993)].

Although the acetic acid produced by the carbonylation of methanol has a relatively high purity, it is known that the acetic acid contains a minute amount of reductive impurities as evaluated by the potassium permanganate test conducted in accordance with JIS K 1351 [see European Patent Publication-A No. 322,215 (published on Jun. 28, 1989)]. The potassium permanganate test is an important industrial test which acetic acid must pass when it is put in various practical uses as a product. Therefore, the removal of the above impurities leading to poor results in this test is of utmost importance.

The conventional purification methods for obtaining commercially suitable high-quality acetic acid capable of meeting the standards include, for example, (a) chemical addition method [for example, addition of an amine, a nonvolatile acid or the like as disclosed in Japanese Patent Publication-B No. 42-6243 (published on Mar. 14, 1967)] and (b) oxidant addition method [for example, addition of peracetic acid as disclosed in Japanese Patent Publication-B No. 48-30615 (published on Sep. 21, 1973)]. However, the above methods require the use of various additives, so that problems arise with respect to handling and aftertreatment. That is, not only is at least simple distillation for separating the additives further required but also there is a potential problem of the additives remaining in the acetic acid as a product. Especially, the oxidant addition method (b) has a potential danger of explosion attributed to a rapid reaction of peroxide remaining unreacted in separating the additives. Therefore, a purification method in which no additives are added is desired.

While, in a distilling method, concentration of a minute amount of impurities to a considerable extent is required for minimizing acetic acid entrained in the separation and disposal of impurities to thereby suppress the purification loss of the acetic acid. Thus, the distillation column must have a considerably large number of plates and a considerably high reflux ratio. Consequently, a considerably large amount of thermal energy is to be consumed, thereby bringing about a problem of gravely pushing up the cost for purification. Therefore, a method of economically removing the above impurities is desired.

DISCLOSURE OF THE INVENTION

Summary of the Invention

Under these circumstances, the present inventors have made extensive studies with respect to the purification of acetic acid which contains a minute amount of impurities composed of at least one component selected from among organoiodine compounds, metalloiodine compounds, iodide ions, unsaturated compounds and carbonyl compounds and which exhibits poor results in the potassium permanganate test. As a result, a distilling method of the present invention which ensures, without the addition of chemicals for separating the impurities, energy-saving economical purification for obtaining high-quality acetic acid which exhibits high results in the potassium permanganate test, has been completed.

That is, the present invention relates to a method for purifying acetic acid containing at least one component selected from the group consisting of organoiodine compounds, metalloiodine compounds, iodide ions, unsaturated compounds and carbonyl compounds as an impurity, which comprises purifying the acetic acid with a distillation column having at least 30 plates by operating the distillation column under a pressure ranging from 40 to 760 mmHg at a reflux ratio of at least 4.

In other words, the present invention relates to a method of purifying acetic acid containing impurities composed of at least one component selected from among organoiodine compounds, metalloiodine compounds, iodide ions, unsaturated compounds and carbonyl compounds, characterized in that the purification is conducted in a distillation column having at least 30 plates and operated under a pressure ranging from 40 to 760 mmHg and a reflux ratio of at least 4 to thereby obtain high-quality acetic acid as a product.

Although the present invention is in principle applicable to any acetic acid, irrespective of its production process, it is advantageously applied especially to the product of carbonylation of methanol or the like performed in the presence of a metal catalyst such as a rhodium catalyst with the use of a cocatalyst of a halide such as an organic halide, as described in G.B. Patent Publication-A No. 1,233,121.

Further scope and applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Detailed Description of the Invention

The production of acetic acid by carbonylation of methanol is performed in the following manner. Methanol and carbon monoxide as the starting compounds are continuously charged in a reactor to conduct a reaction at a given temperature and pressure as described in, for example, U.S. Pat. No. 4,102,922 (published on Jul. 25, 1978). One of the starting compounds is not limited to methanol, but at least one of methyl acetate, dimethyl ether and methanol, a mixture of two or more of them or a mixture of at least one of the above compounds and water may be used. The reaction temperature ranges generally from about 150 to 250° C., preferably from about 180 to 220° C. The total reaction pressure is controlled so as to range from about 15 to 40 kg/cm$^2$G in consideration of the partial pressures of carbon monoxide and hydrogen and the vapor pressures of the liquid components present in the reactor.

The rhodium catalyst which is employed in the carbonylation of methanol may take any form, as far as it can be converted into a complex soluble in the reaction fluid under the reaction conditions. In the reaction fluid, the rhodium concentration ranges from about 200 to 1000 ppm, preferably from about 300 to 600 ppm.

In the carbonylation of methanol, methyl iodide is used as a promoter and is contained in the reaction fluid in a concentration ranging from about 5 to 20% by weight, preferably from about 12 to 16% by weight.

The concentration of water in the reaction fluid is about 10% by weight or below, preferably from 1 to 5% by weight.

The carbonylation of methanol is continuously performed, so that methyl acetate formed by the reaction between methanol as the starting compound and acetic acid is present in the reaction fluid. The amount of methyl acetate is controlled so as to range from about 0.1 to 30% by weight, preferably from about 0.5 to 5% by weight. Also, acetic acid, which is a product and a reaction solvent, is present in the reaction fluid as a main component.

When the carbonylation of methanol is effected under low water content conditions, an iodide salt is added to the reaction fluid for the stabilization of the rhodium catalyst and as a cocatalyst. The above iodide salt is not particularly limited as long as it dissociates into an iodide ion in the reaction fluid. Examples of the iodide salts include alkali metal iodides such as LiI, NaI, KI, RbI and CsI, alkaline earth metal iodides such as BeI$_2$, MgI$_2$ and CaI$_2$ and aluminum-group metal iodides such as BI$_3$ and AlI$_3$. The iodide salt is not limited to these metal iodides, and organic iodides may be used, which include, for example, quaternary phosphonium iodides (such as an adduct of tributylphosphine with methyl iodide or hydrogen iodide and an adduct of triphenylphosphine with methyl iodide or hydrogen iodide) and quaternary ammonium iodides (such as adducts of tertiary amines with methyl iodide or hydrogen iodide, adducts of pyridines with methyl iodide or hydrogen iodide, adducts of imidazoles with methyl iodide or hydrogen iodide, and adducts of imides with methyl iodide or hydrogen iodide). Among them, alkali metal iodides such as LiI are preferred. The iodide salt is used, irrespective of the type of the iodide salt, in an amount of 0.07 to 2.5 mol/l, preferably 0.25 to 1.5 mol/l in terms of iodide ion, i.e., as a molar concentration of iodide ion contained in the reaction fluid.

The crude acetic acid thus formed is purified by an operation such as distillation for removing water. However, after the purification, the acetic acid generally contains, as an impurity, at least one component selected from the group consisting of organoiodine compounds, metalloiodine compounds, iodide ions, unsaturated compounds and carbonyl compounds, as described in European Patent Publication-A No. 322,215 (published on Jun. 28, 1989). Examples of the organoiodine compounds include ethyl iodide, butyl iodide and hexyl iodide. Examples of the unsaturated compounds include acetaldehyde, butyraldehyde, crotonaldehyde and 2-ethylcrotonaldehyde, and products formed by aldol condensation of these aldehydes. It is described in Japanese Patent Publication-A No. 1-211548 that the main components of the impurities are alkyl iodides, various unsaturated compounds such as crotonaldehyde, ethylcrotonaldehyde and 2-methyl-2-pentenal, and carbonyl compounds. These impurities present in minute amounts cause the mark result of the potassium permanganate test of acetic acid to be poor, thereby lowering the commercial value and industrial availability of the acetic acid as a product.

The present inventors have extensively studied with respect to a purification method of the above acetic acid. As a result, they have found that the purification of the above acetic acid by the method of the present invention realizes the economical conversion of the crude acetic acid to a high-quality acetic acid which exhibits high results in the potassium permanganate test.

That is, the present invention comprehends a method of purifying acetic acid containing impurities composed of at least one component selected from among organoiodine compounds, metalloiodine compounds, iodide ions, unsaturated compounds and carbonyl compounds in a process for producing acetic acid which comprises reacting methanol, a mixture of methyl acetate and water or a mixture of methyl acetate, methanol and water with carbon monoxide in a reaction medium containing a rhodium catalyst, water, acetic acid and methyl iodide, characterized in that the purification is conducted in a distillation column having at least 30 plates and operated under a pressure ranging from 40 to 760 mmHg and a reflux ratio of at least 4 to thereby obtain high-quality acetic acid as a product.

Examinations of patent and other documents published heretofore have revealed that the distillation of acetic acid is carried out under atmospheric or a higher pressure [see G.B. Patent Publication-A No. 1,294,432 and U.S. Pat. No. 4,029,553 (published on Jun. 14, 1977)] and that no purification of acetic acid is effected under a reduced pressure. That is, operation under atmospheric or a higher pressure has become a matter of general knowledge in the purification of acetic acid by distillation.

In the present invention, the distillation is effected with a distillation column which can be operated under reduced pressure. Any type of distillation columns customarily employed in separation and purification of solutions, including a packed column, a plate column and a combination thereof, may be used in the present invention as long as the following requirements are met. Generally, a plate column is employed for vacuum distillation.

In the present invention, the acetic acid to be purified, which exhibits poor results in the potassium permanganate test, is fed into the distillation column at its middle and heated in a reboiler. Organic iodides, unsaturated compounds and carbonyl impurities, which may have boiling points lower than that of acetic acid, occasionally together with iodide ion impurities, are concentrated at the top of the column. Some impurities among them may be concentrated at the top of the column as an azeotropic mixture. On the other hand, iodide ion impurities, and organic iodides, unsaturated compounds and carbonyl impurities, which have boiling points higher than that of acetic acid, are concentrated at the bottom of the column.

For achieving the concentration and separation of the above impurities, the distillation column must have a large number of plates and a high reflux ratio is necessitated. The distillation column has at least 30 plates, preferably at least 50 plates. The reflux ratio is at least 4, preferably at least 50.

The high reflux ratio inevitably requires a great amount of thermal energy in the reboiler. However, in the present invention, the distillation is performed under a reduced pressure, so that the boiling points of components in crude acetic acid are lowered. Accordingly, a great amount of thermal energy is not necessitated even when a high reflux ratio is employed. Therefore, in the purification method of the present invention, overhead steam, low-pressure waste steam and the like available from other distillation columns can be used as the heat source for the reboiler of the vacuum distillation column. Thus, little additional thermal energy is necessitated for the purification method of the present invention.

The operating pressure of the vacuum distillation column for use in the present invention ranges from 40 to 760 mmHg, of which an appropriate pressure can be selected by taking into account the temperature of the heat source for use in the reboiler. Especially, it is preferred that the operating pressure ranges from 40 to 400 mmHg, at which the temperature of the bottoms is not higher than the boiling point of water at atmospheric pressure to thereby widen the range of employable heat sources.

The organic iodides, unsaturated compounds and carbonyl impurities, occasionally together with iodide ion impurities, which have been concentrated at the top of the column, are batchwise or continuously withdrawn in small quantities, and wholly or partially recycled to a carbonylation reactor for effective reutilization. On the other hand, the bottoms are batchwise or continuously withdrawn, if necessary, and recycled to the previous step. Alternatively, the components concentrated at the top and the bottom of the column may wholly or partially be disposed of outside the system in order to maintain the quality of acetic acid as a product.

In the present invention, the distillation is conducted at lower temperatures, so that the thermal conversion of acetic acid to, for example, acetic anhydride can be minimized, thereby achieving purification with minimized loss.

Acetic acid as a product is withdrawn in vaporous or liquid form from the distillation column at, for example, the second plate counted from the bottom.

Figure 1A:
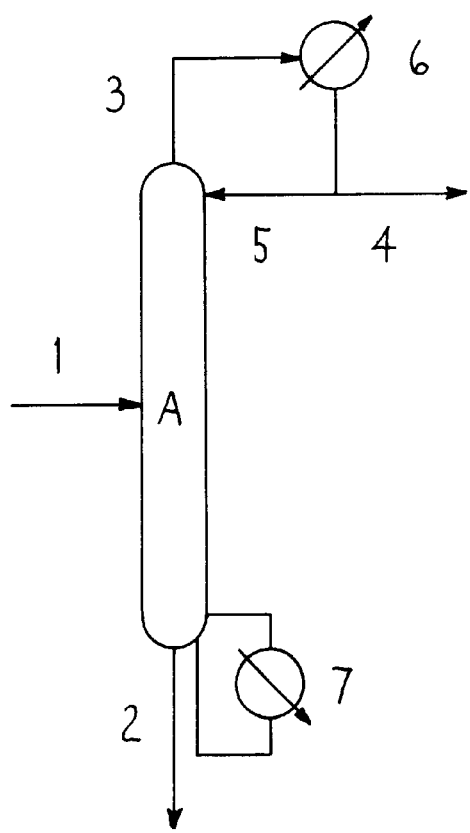
FIG. 1a is a flow diagram showing a step of the conventional acetic acid purification process and FIG. 1b is a flow diagram showing a step of the acetic acid purification process of the present invention.

In the above figures, reference numerals 1 to 5, 8 to 13, 16 to 20 and 23 to 28 are each a line, 6, 14, 21 and 29 are each a condenser, and 7, 15, 22 and 30 are each a reboiler.

DESCRIPTION OF THE PREFERABLE EMBODIMENT

One embodiment of the present invention will be described below with reference to FIGS. 1a, 1b and 2 (FIG. 1a being a referential view) to thereby more clearly demonstrate the availability of the present invention.

Figure 1B:
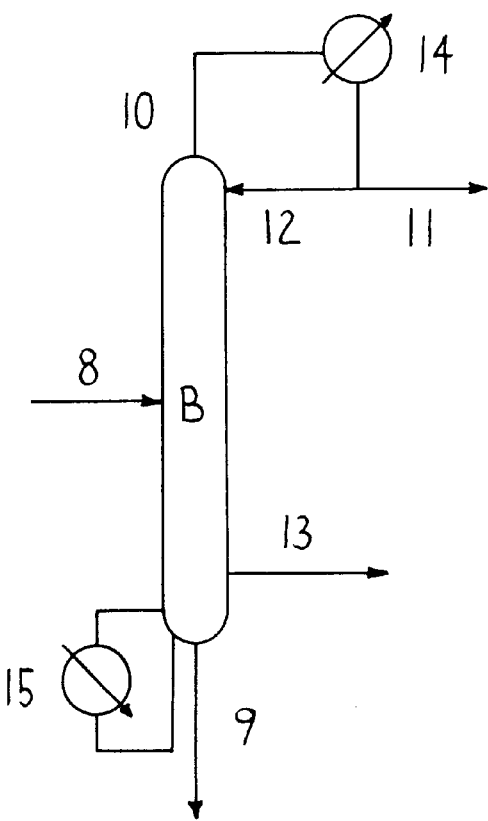

Referring to FIG. 1b, the column B is a vacuum distillation column suitable for use in the present invention. Acetic acid to be purified which has poor results in the potassium permanganate test is charged through a line 8 into the column B at its middle. Overhead steam output from the column B is led through a line 10 into a condenser 14, in which the steam is condensed. Part of the condensate is wholly recycled through a line 11 to a carbonylation reactor or disposed of. Alternatively, part of the condensate is partially recycled through a line 11 to a carbonylation reactor and partially disposed off. The rest of the condensate formed in the condenser 14 is recycled through a line 12 to the column B as a reflux. Bottoms are withdrawn through a line 9. The bottoms are wholly recycled to the previous step or disposed off. Alternatively, the bottoms are partially recycled to the previous step and partially disposed off. The fluid withdrawn through a line 13 is product acetic acid. Alternatively, the fluid is further purified by means of, for example, an ozone treatment.

Referring to FIG. 1a, the column A is a distillation column as described in U.S. Pat. No. 4,029,553 (published on Jun. 14, 1977) which is used for removing, through a line 2, a heavy fraction from acetic acid produced by the carbonylation of methanol. This column A constitutes a step of the conventional acetic acid purification process and is operated under atmospheric or higher pressure.

Acetic acid to be purified in column A is charged through a line 1 into column A at its middle. Overhead steam output from the column A is led through a line 3 into a condenser 6, condensed there, and fed through a line 4 to the subsequent purification step. As shown in FIG. 1a, part of the flow from the condenser 6 is recycled through a line 5 to column A as a reflux.

Figure 2:
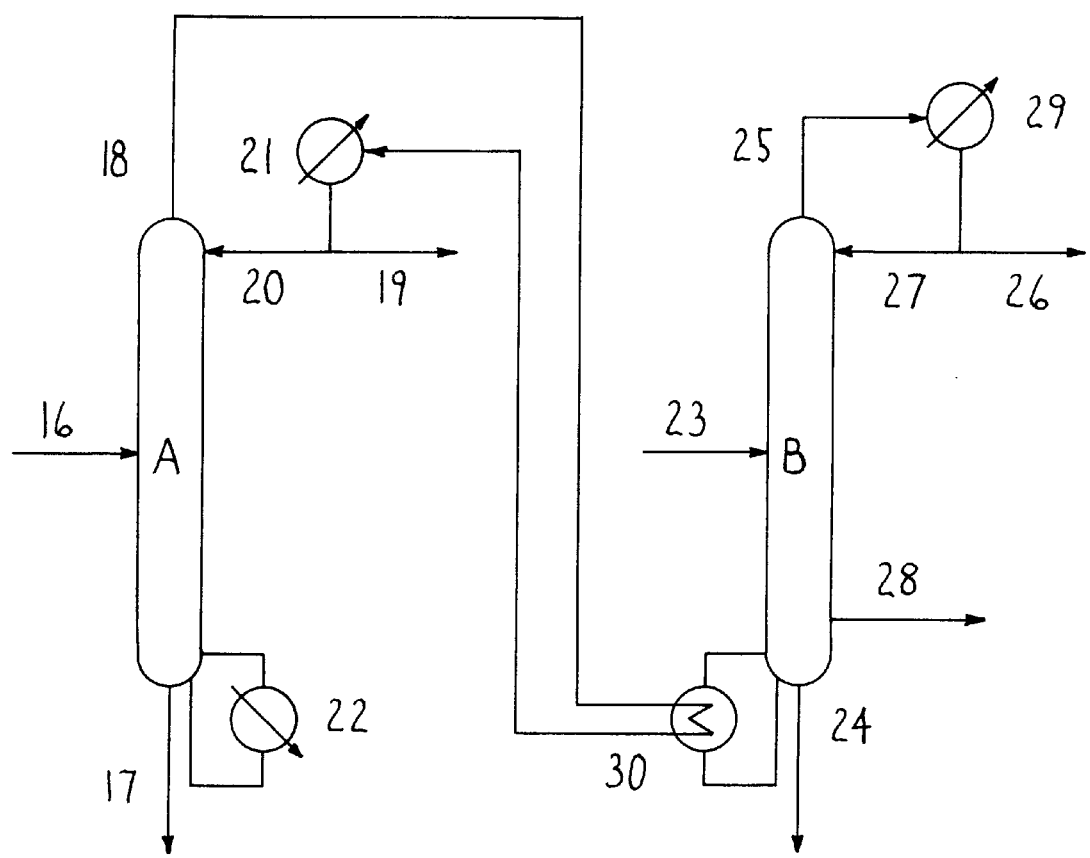
FIG. 2 is a flow diagram showing the process according to the acetic acid purification method of the present invention.

In the present invention, as shown in FIG. 2, the overhead steam led through a line 18 of column A can be used as a heat source for a reboiler 30 of column B. When column A is operated at about 1.03 kg/cm$^2$, the temperature of the overhead is 118° C., which is satisfactory for use as heat source for the column B. Therefore, in the present invention, acetic acid produced by the carbonylation of methanol can be purified into high-quality acetic acid which rates highly in the potassium permanganate test with only a small increase in the purification energy required in conventional acetic acid purification processes through the use of the overhead steam output from distillation column A process as the heat source for the reboiler of vacuum distillation column B for use in the present invention.

EXAMPLES

The availability of the present invention will now be described with reference to the following examples which should not be considered to limit the scope of the present invention.

Example 1

An acetic acid purification experiment was conducted with the use of a 50-plate Oldershaw distillation column (a type of plate column).

The pressure of the distillation column was controlled so as to be 400 mmHg at the top of the column, where the temperature was about 90° C. Acetic acid to be charged was fed at a flow rate of about 1.1 kg/hr to the 23rd plate counted from the bottom of the column. Purified acetic acid was withdrawn in vaporous form from a section very close to the bottom of the column. The distillation column was operated at a reflux ratio of about 150. Bottoms and overhead were continuously withdrawn outside the system at flow rates equal to about 1% and about 0.8% of the charge flow rate, respectively. Continuous operation under these conditions resulted in an improvement in the results of the potassium permanganate test from 125 min of the charged acetic acid (this poor value being attributed to the inclusion of at least crotonaldehyde, ethylcrotonaldehyde and 2-methyl-2-pentenal) to at least 240 min of the purified acetic acid.

Example 2

Methanol was continuously carbonylated at 185° C. in the presence of carbon monoxide in a reaction medium consisting essentially of 14% by weight of methyl iodide, 8% by weight of water, 1.6% by weight of methyl acetate, 71% by weight of acetic acid, 5% by weight of lithium iodide and 400 ppm of rhodium, with the use of a continuous withdrawal autoclave (a carbonylation reactor), thereby producing acetic acid. The obtained reaction fluid was introduced into an evaporator, in which the reaction fluid was separated into a volatile phase containing the product and a nonvolatile phase containing the catalyst. The volatile phase was successively distilled for removing a low-boiling fraction, for dehydration and for removing a high-boiling fraction, thereby obtaining acetic acid. This acetic acid contained at least crotonaldehyde, ethylcrotonaldehyde and 2-methyl-2-pentenal, so that the potassium permanganate test result of the acetic acid was as poor as 110 min.

A purification experiment was conducted for this acetic acid with the use of the same distillation column as that of Example 1 and under the same operating conditions as those of Example 1. The resultant purified acetic acid had the potassium permanganate test result improved to at least 240 min.

Example 3

The heat balance was calculated with respect to the operation of the plant of FIG. 2.

Column A of FIG. 2, i.e., the column for removing a heavy fraction from the crude acetic acid, could be operated according to the balance of Table 1. The operating pressure was 1.03 kg/cm$^2$, and the column top temperature was 118° C.

TABLE 1

| | Flow rate |
|---|---|
| line 16 | 34.1 kg/hr |
| line 17 | 1% of line 16 |
| line 20 | 56% of line 18 |
| line 19 | line 16 − line 17 |

From the above, the flow rate and temperature of the overhead steam (line 18) output from column A which can be used as a heat source for the reboiler of the column B are 76.7 kg/hr and 118° C., respectively. In the heat balance, the amount of the fluid (i.e., the overhead steam) is expressed in terms of acetic acid because the amount of the components other than acetic acid is very minute in the fluid. The latent heat of evaporation of acetic acid is 97 kcal/kg, so that a quantity of heat of 7.4×10$^3$ kcal/hr can be obtained from the overhead steam output from the column A.

According to the procedure of Example 1 of the present invention, column B of FIG. 2 can be operated in accordance with the balance specified in Table 2. The operating pressure at the column top is 400 mmHg and the column bottom temperature is 95° C.

TABLE 2

| | flow rate |
|---|---|
| line 23 | 33.8 kg/hr |
| line 24 | 0.34 kg/hr |
| line 26 | 0.26 kg/hr |
| line 27 | 39 kg/hr |

In this instance, the quantity of heat needed for the reboiler of the column B is 7.1×10$^3$ kcal/hr.

Hence,

| quantity of heat carried by overhead steam from column A | > | quantity of heat needed for reboiler of column B. |
|---|---|---|

Therefore, when column B of FIG. 1b according to the present invention is added to the purification system including column A of FIG. 1a and when the process of FIG. 2 is employed, column B can be operated without the need of additional thermal energy to thereby obtain a high-quality acetic acid.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What we claim is:

1. A method for purifying a crude acetic acid product mixture, which comprises the steps of: purifying a crude acetic acid product mixture containing at least one impurity selected from the group consisting of unsaturated compounds and carbonyl compounds in a first distillation column operated at atmospheric or an increased pressure and then purifying the mixture in a second distillation column having at least 30 plates and operated at a pressure ranging from 40 to 760 mmHg and a reflux ratio of at least four, wherein overhead vapor from the first column is used as the heat source for a reboiler of the second column and the pressure of the second column is less than the pressure of the first column.

2. The method as claimed in claim 1, in which an acetic acid product in the form of a vapor or liquid is removed from the second column.

3. The method as claimed in claim 1, in which the at least one impurity essentially consists of crotonaldehyde, ethylcrotonaldehyde and 2-methyl-2-pentenal.

4. The method of claim 1, wherein the second distillation column operates at a pressure of from 40 to 400 mm Hg.

5. The method of claim 1, wherein the crude acetic acid product mixture is formed by subjecting crude acetic acid to distillation to remove water therefrom.

6. The method of claim 1, wherein said second distillation column has at least 50 plates and operates at a reflux ratio of at least 50.

7. In a method of purifying a crude acetic acid product mixture produced by reacting a mixture of methanol or methyl acetate and water or a mixture of methyl acetate, methanol and water and carbon monoxide in a reaction solvent comprising a rhodium catalyst, water, acetic acid and methyl iodide to form a crude acetic acid product mixture;

the improvement comprising the steps of: purifying the crude acetic acid product mixture, in which is contained at least one impurity selected from the group consisting of unsaturated compounds and carbonyl compounds, in a first distillation column operating at atmospheric or an increased pressure and then purifying the crude acetic acid product mixture in a second distillation column comprising at least 30 plates and operated at a pressure ranging from 40 to 760 mmHg and a reflux ratio of at least 4, wherein overhead vapor from the first column is used as the heat source for a reboiler of the second column and the pressure of the second column is lower than the pressure of the first column.

8. The method as claimed in claim 7, in which all or a portion of a distillate from the top of the second column is recycled to a carbonylation reactor.

9. The method as claimed in claim 7, in which an acetic acid product in the form of a vapor or liquid is removed from the second column.

10. The method as claimed in claim 7, in which the at least one impurity essentially consists of crotonaldehyde, ethyl crotonaldehyde and 2-methyl-2-pentenal.

11. The method of claim 7, wherein the second distillation column operates at a pressure of from 40 to 400 mm Hg.

12. The method of claim 7, wherein the crude acetic acid product mixture is formed by subjecting crude acetic acid to distillation to remove water therefrom.

13. The method of claim 7, wherein said second distillation column has at least 50 plates and operates at a reflux ratio of at least 50.

* * * * *